United States Patent
Derkx et al.

(10) Patent No.: US 6,607,904 B2
(45) Date of Patent: Aug. 19, 2003

(54) PEPTIDYL PROLYL CIS-TRANS ISOMERASES

(75) Inventors: Patrick M. F. Derkx, Copenhagen (DK); Susan M. Madrid, Vedbaek (DK)

(73) Assignee: Danisco A/S, Copenhagen K (DK)

( * ) Notice: Subject to any disclaimer, the term of this patent is extended or adjusted under 35 U.S.C. 154(b) by 0 days.

(21) Appl. No.: 10/043,142

(22) Filed: Jan. 14, 2002

(65) Prior Publication Data
US 2002/0150969 A1 Oct. 17, 2002

Related U.S. Application Data

(62) Division of application No. 09/806,399, filed as application No. PCT/IB99/01669 on Sep. 30, 1999.

(30) Foreign Application Priority Data

Sep. 30, 1998 (GB) .............................................. 9821198

(51) Int. Cl.$^7$ ................................................ C12N 9/90
(52) U.S. Cl. ...................................................... 435/233
(58) Field of Search ........................................ 435/233

(56) References Cited

U.S. PATENT DOCUMENTS

| 6,127,148 A | * 10/2000 | Carlow et al. ............. 435/69.1 |
| 2001/0034045 A1 | 10/2001 | Penttila et al. | |

FOREIGN PATENT DOCUMENTS

| EP | 0413440 | * | 2/1991 |
| EP | 0 455 316 A2 | | 11/1991 |
| WO | WO 94/23040 | * | 10/1994 |
| WO | WO 94/24292 A2 | | 10/1994 |
| WO | WO 95/10616 A2 | | 4/1995 |
| WO | WO 96/01323 A1 | | 1/1996 |
| WO | WO 96/29416 A1 | | 9/1996 |
| WO | 97/38123 | | 10/1997 |

OTHER PUBLICATIONS

Hornbogen, T., et al. (1992) Biochem. Biophys. Res. Comm. 187(2), 791–796.*
Spik, G., et al. (1993) Accession No. HUMSCYLP.*
Corini, P, et al. (1993) Accession No. CHKSCYCLO.*
Kieffer, L.J., et al. (1993) Accession No. BOVCYC40B.*
Chen et al., "A Cyclophilin from the Polycentric Anaerobic Rumen Fungus Orpinomyces sp. Strain PC–2 is Highly Homologous to Vertebrate Cyclophilin B", Proc. Natl. Acad. Sci. USA, vol. 92, No. 7, pp. 2587–2591. 1995, Biochemistry, Natl. Academy of Science, Washington, XP002129590.
Hornbogen et al., "Two New Cyclophilins from Fusarium sambucinum and Aspergillus niger", Biochem. & Biophys. Research Comm., vol. 187, No. 2, pp. 791–796, 1992, Academic Press, Inc.
Tsuchiya et al., "High level expression of the synthetic human lysozyme gene in Aspergillus oryzae," Applied Microbiology and Biotechnology (1992), vol. 38, pp. 109–114.
Schonbrunner et al., "Catalysis of protein folding by cyclophilins from different species," J. Biol. Chem. (1991), vol. 266, No. 6, pp. 3630–3635, The American Society for Biochemistry and Molecular Biology, Inc..
Jeenes et al., "Isolation and characterisation of a novel stress–inducible PDI–family gene from Aspergillus niger," Gene (1997), vol. 193, pp. 151–156.
Bergsma et al., "The Cyclophilin Multigene Family of Peptidyl–Prolyl Isomerases," J. Biol. Chem. (1991), vol. 266, No. 34, pp. 23204–23214, The American Society for Biochemistry and Molecular Biology, Inc.
Rouviere et al., "SurA, a periplasmic protein with peptidyl–prolyl isomerase activity, participates in the assembly of outer membrane porins," Genes & Dev. (1996), vol. 10, pp. 3170–3182, Cold Spring Harbor Laboratory Press, ISSN: 0890–9369..
Wang et al., "Enzymes as chaperones and chaperones as enzymes," FEBS lett. (1998), vol. 425, pp. 382–382, Federation of European Biochemical Societies.
Gurr et al, "The Structure and organization of nuclear genes of filamentous fungi," Gene Structure in Eukaryotic Microbes, (1987), pp. 93–139, IRL Press, Oxford.
Rambosek et al., "Recombinant DNA in filamentous fungi: Progress and Prospects" CRC Crit. Rev. Biotechnol. (1987), vol. 6, Issue 4, pp. 357–393.
Davies, "Heterologous gene expression and protein secretion in Aspergillus" In: Martinelli et al., Aspergillus: 50 years on—Progress in industrial microbiology, (1994), vol. 29, pp. 527–560, Elsevier Amsterdam.
Ballance, "Transformation systems for filamentous funcgi and an Overview of Fungal Gene structure," In Leong et al. (editors) Molecular Industrial Mycology: Systems and Applications for Filamentous Fungi (1991), pp. 1–29, Marcel Dekker Inc. New York.
Turner, "Vectors for genetic manipulation" In Martinelli et al. (editors) Aspergillus: 50 years on: Progress in industrial microbiology (1994), vol. 29, pp. 641–666, Elsevier Amsterdam.
Broekhuijsen et al., "Secretion of heterologous proteins by Aspergillus niger: Production of active human interleukin–6 in a protease–deficient mutant by KEX2–like preocessing of a glucoamylase–hIL6 fusion protein," J. Biotechnol (1993), vol. 31, pp. 135–145, Elsevier Science Publishers B.V..
Myers et al. "Optimal Alignments in Linear Space" CABIOS (1988), vol. 4, No. 1, pp. 11–17, IRL Press Limited, Oxford, England.

(List continued on next page.)

Primary Examiner—Charles L. Patterson, Jr.
(74) Attorney, Agent, or Firm—Foley & Lardner

(57) ABSTRACT

The present invention provides a method for producing a secretable polypeptide in a host cell. In the method, a peptidyl prolyl cis-trans isomerase is overexpressed in a host cell, thereby increasing the yield of the secreted polypeptide.

7 Claims, 7 Drawing Sheets

OTHER PUBLICATIONS

Wilbur et al., "Rapid similarity searches of nucleic acid and protein data banks," *Proc. Natl. Acad. Sci. USA* (1983) vol. 80, pp. 726–730.

Needleman et al. "A general method applicable to the search for similarities in the amino acid sequences of two proteins," *J. Mol. Biol.* (1970), vol. 48, pp. 443–453.

Smith et al. "Statistical characterization of nucleic acid sequence functional domains," *Nucleic Acids Res.* (1983), vol. 11, No. 7, pp. 2205–2220, IRL Press Limited, Oxford, England.

Feng et al., "Progressive sequence alignment as a prerequisite to correct phylogenetic trees," *J. of Molec. Evol.* (1987), vol. 25, pp. 351–360, Springer–Verlag New York Inc.

Higgins et al., "Fast and sensitive multiple sequence alignment on a microcomputer" *CABIOS* 5: (1989), vol. 5, No. 2, pp. 151–153, IRL Press.

Thompson et al., "ClusterW: improving the sensitivity of progressive multiple sequence alignment through sequence weighing, positions–specific gap penalties and weight matrix choice" *Nucleic Acid Res.* (1994), vol. 22, No. 22, pp. 4673–4680, Oxford University Press.

Devereux et al. "A comprehensive set of sequence analysis program for the VAX" *Nucl. Acids Res.* (1984), vol. 12, No. 1, pp. 387–395, IRL Press Limited, Oxford, England.

Sambrook et al. Eds. *Molecular Cloning: A Laboratory Manual* (1989) Cold Spring Harbor Laboratory Press, New York (Index Only).

Ausubel et al. Eds. *Current Protocols in Molecular Biology* John Wiley & Sons, Inc. (Index Only).

\* cited by examiner

FIG. 2

```
A.niger        1   .MNFKNIFLSFFFVLAVGLALVHAEDAQPRGPRITSKVFFDIEHGDKPLGRVVLG
Orpinomyces    1   ......MNFSIKSVIFLAIVALATLVSASTNPKVINKVFFDIKQGDKDLGRIVLG
M.musculus     1   MKALVAATALG.PALLLLLPAASRADERKKGPKVTAKVFFDLRVGEEDAGRVVIG
H.sapiens      1   MKVLLAAALIAGSVFFLLLPGPSAADEKKKGPKVTVKVYFDLRIGDEDVGRVIFG A.niger       55   LYGKTVPKIAENFRALATGEKGFGYEGSIFHRVIKDFMIQGGDFTRGDGTGGKSI
Orpinomyces   50   LYGEVPKTVENFRALATGEKGFGYKNSKFHRVIKDFMIQGGDFTRGDGTGGKSI
M.musculus    55   LFGKTVPKTVENFVALATGEKGFGFKGSKFHRVIKDFMIQGGDFTRGDGTGGKSI
H.sapiens     56   LFGKTVPKTVDNFVALATGEKGFGYKNSKFHRVIKDFMIQGGDFTRGDGTGGKSI A.niger      110   YGEKFADENFKLRHTRKGLLSMANAGKDTNGSQFFITTVPTPMLDGRHVVFGEV
Orpinomyces  105   YGERFADENFKLRIHTGPGILSMANAGRDTNGSQFFITTVTISWLDGRHVVFGKV
M.musculus   110   YGDRFPDENFKLKIHYGPGWVSMANAGKDTNGSQFFITTVKTAMLDCKHVVFGKV
H.sapiens    111   YGERFPDENFKLKHYGPGWVSMANAGKDTNGSQFFITTVKTAMLDCKHVVFGKV A.niger      164   LECYEIVACIENVPKGRSDRPVETVKIVKSGELESEDKAGEKGSSHEEL
Orpinomyces  159   IEGMDVVTAIETTKTLPGDRPATPVIIADCGELPVS.....NNNDAKAEL
M.musculus   164   LEGMDVVRKVENTKTDSRDKPLKDVIIADCGTIEVE.....KPFAIAKE.
H.sapiens    165   LEGMEVVRKVESTKTDSRDKPLKDVIIADCGKIEVE.....KPFAIAKE.
```

FIG. 3

```
A.niger      MNFKNIFLSF FFVLAVGLAL VHAEDAQPRG PKITSKVFFD IEHGDKPLGR
             |||        |    |    |  ||            || | || || |  ||| |||
Orpinomyces  MNFS..IKSV IFLAIVALAT LVSASTN... PKVTNKVYFD IKQGDKDLGR A.niger      VVLGLYGKTV PKTAENFRAL ATGEKGFGYE GSTFHRVIKD FMIQGGDFTR
             ||||||  |  ||| |||||| |||||| ||     | ||||||| |||||||||
Orpinomyces  IVLGLYGEVV PKTVENFRAL ATGEKGYGYK NSKFHRVIKD FMIQGGDFTR A.niger      GDGTGGKSIY GEKFADENFK LRHTRKGLLS MANAGKDTNG SQFFITTVPT
             |||||||||| ||  ||||||| ||||   | ||  ||||| |||| ||||||||| |
Orpinomyces  GDGTGGKSIY GERFADENFK LRHTGPGILS MANAGRDTNG SQFFITTVTT A.niger      PWLDGRHVVF GEVLEGYEIV AQIENVPKGR SDRPVETVKI VKSGELESED
              ||||||||| |  ||    |    ||      |||   | |      |||
Orpinomyces  SWLDGRHVVF GKVIEGMDVV TAIETTKTLP GDRPATPVII ADCGELPVSN A.niger      KAGEKGSSHE EL
                         ||
Orpinomyces  ....NNDAKA EL
```

Identity: 134 amino acids (63,21%)

PEPTIDYL PROLYL CIS-TRANS ISOMERASES

This is a Divisional of application Ser. No. 09/806,399, filed on Aug. 1, 2001 which is a 371 of PCT/IB99/01669, filed Sep. 30, 1999.

The present invention relates to a novel enzyme. In particular, the invention relates to a novel cyclophilin-like peptidyl prolyl cis-trans isomerase.

In most protein over-production strategies, strong promoters capable of directing very high levels of transcription are used to over-express genes encoding heterologous and homologous proteins. Limitations in protein secretion are likely to be due to bottlenecks at the translational and post-translational levels (Tsuchiya, K. et al., (1992) Applied Microbiology and Biotechnology 38:109–114). Proper folding of the protein is required for export competence. Overexpressed heterologous proteins may fold improperly and then be degraded during protein traffic through the secretory pathway. Therefore, the correction of folding defects is desirable in order to increase protein secretion.

The folding of a protein is catalysed by an number of factors, including two isomerase families, namely protein disulphide isomerase, catalysing disulphide bond formation, and peptidyl prolyl cis-trans isomerase, catalysing the isomerisation of Xaa-Proline bonds.

Overexpression of protein disulphide isomerase in S. cerevisiae results in an increase in secretion of human platelet-derived growth factor (Robinson et al., 1994). However, the overproduction of A. niger protein disulphide isomerase did not result in an increase in secretion of hen egg white lysozyme (HEWL) or glucoamylase (Ngiam C., Jeenes, D. J. J., Punt, P. J., van den Hondel, C. A. M. J. J., Archer, D. A. (1998); Characterisation of a foldase, PDIA, in the protein secretory pathway of Aspergillus niger, submitted.)

One of the slowest steps in protein folding is the cis-trans isomerisation of Xaa-proline bonds. This isomerisation is markedly accelerated when peptidyl prolyl cis-trans isomerases are present. Peptidyl prolyl cis-trans isomerases of the cyclophilin family from different organisms have been shown to possess foldase activity in vitro (Schönbrunner E. R., Mayer S., Tropschug M., Fischer G., Takahashi N., Schmid, F. (1991); Catalysis of protein folding by cyclophilins from different species. J Biol Chem 266: 3630–3635). These isomerases are inhibited by the immuno-suppressant drug cyclosporin A. The effects on secretion of beterologous peptides by overexpression of peptidyl prolyl cis-trans isomerases are however not known in the prior art.

Proteins active in the E.R. are targeted to this compartment by a carboxy terminal extension of 4 amino acids. In A. niger HDEL (SEQ ID NO: 7); and KDEL (SEQ ID NO: 9) have been reported to function as an E.R. retention signal (Jeenes D..J., et al., (1997) Gene 193:151–156).

SUMMARY OF THE INVENTION

In a first aspect of the present invention, there is provided a method for producing a secretable polypeptide in an host cell, comprising overexpressing a peptidyl prolyl cis-trans isomerase in the cell, thereby increasing the yield of the secreted polypeptide.

In a second aspect, the invention relates to a polypeptide possessing foldase activity characterised by having a capability to catalyse the cis-trans isomerisation of a peptide bond on the N terminal side of proline residues in polypeptides, having a signal sequence at the N-terminus and an endoplasmic reticulum retention signal at the C-terminus, and a molecular weight of 20.7 kDa and a deduced isoelectric point of 6.27.

In a third aspect, the invention relates to a polypeptide possessing foldase activity characterised by having a capability to catalyse the cis-trans isomerisation of a peptide bond on the N terminal side of proline residues in polypeptides, encoded by a nucleic acid capable of hybridising under conditions of low, medium or high stringency with a 17 base oligonucleotide derived from SEQ ID No. 1.

In a fourth aspect, the invention relates to a polypeptide possessing foldase activity characterised by having a capability to catalyse the cis-trans isomerisation of a peptide bond on the N terminal side of proline residues in polypeptides, encoded by a nucleic acid capable of hybridising under conditions of low, medium or high stringency with a 20 base oligonucleotide derived from SEQ ID No. 2.

In a fifth aspect, the invention relates to a polypeptide possessing foldase activity characterised by having a capability to catalyse the cis-trans isomerisation of a peptide bond on the N terminal side of proline residues in polypeptides, which is at least 40% homologous to SEQ. ID. No. 2.

BRIEF DESCRIPTION OF THE DRAWINGS

FIG. 2 shows an alignment of the cypB gene (SEQ ID NO: 5); with peptidyl cis-trans isomerases from Orpinomyces, M. musculus and H. sapiens (SEQ ID NOS: 10–12. respectively, in order of appearance).

FIG. 3 shows an optimised alignment between the cypB gene (SEQ ID NO: 5) and the Orpinimyces PPI gene (SEQ ID NO: 10).

DETAILED DESCRIPTION OF THE INVENTION

Figure 1:
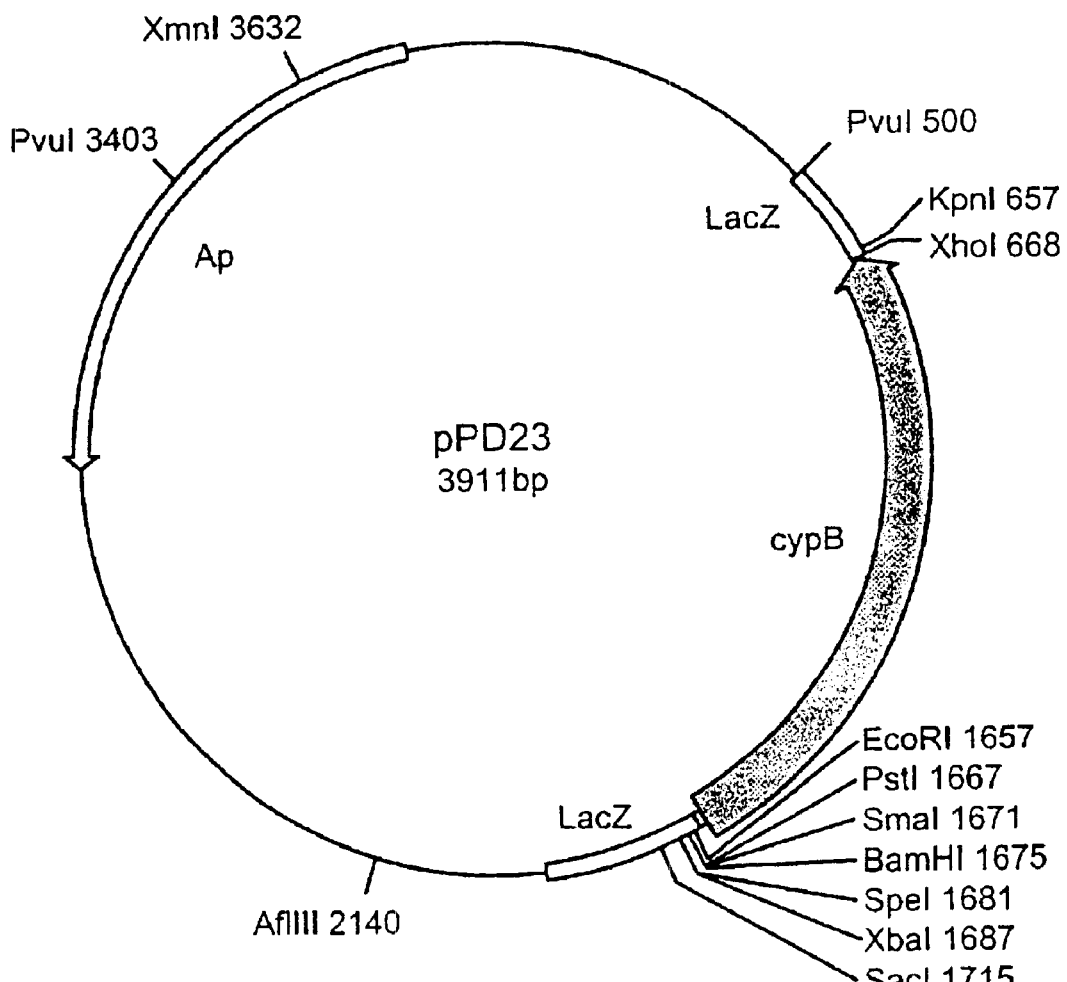
FIG. 1 is a restriction map of plasmid pPD23, which encodes A. niger cypB.

The present invention relates to the overexpression of a peptidyl-prolyl cis-trans isomerase polypeptide (PPI) to increase the expression of secreted polypeptides from host cells. It has been found that increasing levels of PPI in cells is effective to facilitate secretion of polypeptides from the cell. PPI is believed to prevent the retention of polypeptide products in the ER, and their subsequent degradation, by reducing the level of misfolding thereof. Thus, the invention is particularly suitable for increasing the yield of secreted polypeptides from cells.

As used herein, the term "peptidyl-prolyl cis-trans isomerase" polypeptide (PPI) is used to denote an enzyme which is capable of catalysing the cis-trans isomerisation of a peptide bond on the N terminal side of proline residues in polypeptides. PPIs are ubiquitous, and several examples are known in the art. Examples include cyclophilin (see, for example, Bergsma et al. (1991) J. Biol. Chem. 266:23204–23214), parvulin, SurA (Rouviere and Gross, (1996) Genes Dev. 10:3170–3182) and FK506 binding proteins FKBP51 and FKBP52. PPI is responsible for the cis-trans isomerisation of peptidyl-prolyl bonds in polypeptides, thus promoting correct folding. The invention includes any polypeptide having PPI activity. This includes chaperone polypeptides, or fragments thereof, which may possess PPI activity (Wang & Tsou, (1998) FEBS lett. 425:382–384). Preferably, the invention relates to PPI polypeptides of the cyclophilin family.

Advantageously, the host cells are transformed host cells which express a heterologous gene product. Particularly in cases where the heterologous gene product is overexpressed, the tendency for the resulting polypeptides to be misfolded, and thus degraded in the ER as set forth above, is increased. Under these circumstances, therefore, overexpression of PPI in accordance with the invention is highly advantageous.

However, the invention may also be used to increase the production of homologous polypeptides in host cells. For example, the invention is useful where transcription of homologous polypeptides is increased, as a result of an increase in cell activity, caused by natural biological processes or by administration of agents capable of up regulating gene transcription. Moreover, cells may be transformed with a expression systems capable of a causing upregulation of the endogenous genes, for example expression systems encoding transcription factors which are active on endogenous promoters, Similarly, upregulation of PPI expression may be achieved by increasing the expression of endogenous PPI or by transforming the host cell with a coding sequence capable of producing PPI at elevated levels. Advantageously, host cells are transformed with a PPI-encoding sequence.

In a preferred embodiment, therefore, the invention relates to a method for producing a secretable polypeptide in a host cell, comprising cotransfecting the cell with a first coding sequence encoding the polypeptide and a second coding sequence encoding a peptidyl prolyl cis-trans isomerase.

Advantageously, the invention relates to a method for expressing a secretable polypeptide in a host cell, comprising the steps of:

a) transforming the cell with a coding sequence expressing a peptidyl prolyl cis-trans isomerase according to the invention;

b) transforming the cell with a coding sequence expressing a desired polypeptide; and c) culturing the cell to produce the polypeptide.

As used herein, transfection and transformation are considered equivalent, and include any form of insertion of DNA into cells, including viral transduction, electroporation and conventional transfection techniques. The coding sequences encoding peptidyl prolyl cis-trans isomerase and the desired polypeptide may be inserted into the cells on vectors, or independently as naked DNA. The use of vectors is preferred. Where the peptidyl prolyl cis-trans isomerase and the desired polypeptide are present on separate vectors, either one of the separate vectors may be inserted into the host cell before the other. The order of insertion is not important, as long as increased levels of peptidyl prolyl cis-trans isomerase are obtained in the host cell during the expression of the desired polypeptide.

Advantageously, the peptidyl prolyl cis-trans isomerase and the desired polypeptide may be present on the same vector.

Preferably, host cells may be constructed wherein a coding sequence expressing peptidyl prolyl cis-trans isomerase is integrated into the host cell and genome. This can be achieved using an integrating expression vector to transform the cell with the said coding sequence.

As noted above, the coding sequence expressing the peptidyl prolyl cis-trans isomerase is preferably incorporated into a suitable vector. As used herein, vector (or plasmid) refers to discrete elements that are used to introduce heterologous DNA into cells for either expression or replication thereof. Selection and use of such vehicles are well within the skill of the artisan. Many vectors are available, and selection of appropriate vector will depend on the intended use of the vector and the host cell to be transformed with the vector. Each vector contains various components depending on its function and the host cell for which it is compatible. The vector components generally include, but are not limited to, one or more of the following: an origin of replication, one or more marker genes, an enhancer element, a promoter, a transcription termination sequence and a signal sequence.

Most expression vectors are shuttle vectors, i.e. they are capable of replication in at least one class of organisms but can be transfected into another class of organisms for expression. For example, a vector may be cloned in E. coli and then the same vector is transfected into yeast or other fungal cells even though it is not capable of replicating independently of the host cell chromosome. DNA can also be amplified, for example by PCR, and be directly transfected into the host cells without any replication component.

Advantageously, an expression vector may contain a selection gene, also referred to as selectable marker. This gene encodes a protein necessary for the survival or growth of transformed host cells grown in a selective culture medium. Host cells not transformed with the vector containing the selection gene will not survive in the culture medium. Typical selection genes encode proteins that confer resistance to antibiotics and other toxins, e.g. ampicillin, neomycin, methotrexate or tetracycline, complement auxotrophic deficiencies, or supply critical nutrients not available from complex media.

As to a selective gene marker appropriate for yeast and other fungal organisms, any marker gene can be used which facilitates the selection for transformants due to the phenotypic expression of the marker gene. Suitable markers for yeast are, for example, those conferring resistance to antibiotics G418, hygromycin or bleomycin, or provide for prototrophy in an auxotrophic yeast mutant, for example the URA3, LEU2, LYS2, TRP1, or HIS3 gene.

Since the replication of vectors is conveniently done in E. coli, an E. coli genetic marker and an E. coli origin of replication are advantageously included. These can be obtained from E. coli plasmids, such as pBR322, Bluescript© vector or a pUC plasmid, e.g. pUC18 or pUC19, which contain both E. coli replication origin and E. coli genetic marker conferring resistance to antibiotics, such as ampicillin.

Expression and cloning vectors usually contain a promoter that is recognised by the host organism and is operably linked to nucleic acid encoding peptidyl prolyl cis-trans isomerase. Such a promoter may be inducible or constitutive. The promoters are operably linked to DNA encoding the peptidyl prolyl cis-trans isomerase by removing the promoter from the source DNA by restriction enzyme digestion and inserting the isolated promoter sequence into the vector. Both the native promoter sequence and many heterologous promoters may be used to direct amplification and/or expression of the peptidyl prolyl cis-trans isomerase coding sequence. The term "operably linked" refers to a juxtaposition wherein the components described are in a relationship permitting them to function in their intended manner. A control sequence "operably linked" to a coding sequence is ligated in such a way that expression of the coding sequence is achieved under conditions compatible with the control sequences.

Suitable promoting sequences for use with yeast hosts may be regulated or constitutive and are preferably derived from a highly expressed fungal gene. Fungal promoters are known in the literature (for example, see Gurr, et al., (1987) The structure and organisation of nuclear genes of filamentous fungi. In Kinghorn, J. R. (ed), Gene Structure in Eukaryotic Microbes, IRL Press, Oxford, pp. 93–139). Yeast promoters may also be used, such as the promoter of the yeast TRP1 gene, the ADHI or ADHII gene, the acid phosphatase (PH05) gene, a promoter of the yeast mating pheromone genes coding for the a- or α-factor or a promoter derived from a gene encoding a glycolytic enzyme such as the promoter of the enolase, glyceraldehyde-3-phosphate dehydrogenase (GAP), 3-phospho glycerate kinase (PGK), hexokinase, pyruvate decarboxylase, phosphofructokinase, glucose-6-phosphate isomerase, 3-phosphoglycerate mutase, pyruvate kinase, triose phosphate isomerase, phosphoglucose isomerase or glucokinase genes, the *S. cerevisiae* GAL 4 gene, the *S. pombe* nmt 1 gene or a promoter from the TATA binding protein (TBP) gene. Furthermore, it is possible to use hybrid promoters comprising upstream activation sequences (UAS) of one yeast gene and downstream promoter elements including a functional TATA box of another yeast gene, for example a hybrid promoter including the UAS(s) of the yeast PH05 gene and downstream promoter elements including a functional TATA box of the yeast GAP gene (PH05-GAP hybrid promoter). A suitable constitutive PH05 promoter is e.g. a shortened acid phosphatase PH05 promoter devoid of the upstream regulatory elements (UAS) such as the PH05 (−173) promoter element starting at nucleotide −173 and ending at nucleotide −9 of the PH05 gene.

In connection with the present invention, the use of fungal organisms, such as a filamentous fungi, for example those used in the biotechnology industry; preferably Aspergillus, Trichoderma, Neurospora, Mucor or Penicillium, is preferred. More specifically, preferred host organisms include *A. nidulans, A. tubigensis, A. sojae, A. awamori, A. oryzae, A. japonicus, A. aculeatus, N. crassa, T. reesei* and *T. viride*. A preferred host organism for the expression of the nucleic acid constructs of the present invention and/or for the preparation of the heterologous polypeptides according to the present invention is an organism of the genus Aspergillus, advantageously *Aspergillus niger*. In this regard, a transgenic Aspergillus according to the present invention can be prepared by following the teachings of Rambosek, J. and Leach, J. 1987 (Recombinant DNA in filamentous fungi: Progress and Prospects. CRC Crit. Rev. Biotechnol. 6:357–393), Davis R. W. 1994 (Heterologous gene expression and protein secretion in Aspergillus. In: Martinelli S. D., Kinghorn J. R. (Editors) Aspergillus: 50 years on. Progress in industrial microbiology vol 29. Elsevier Amsterdam 1994. pp 525–560), Ballance, D. J. 1991 (Transformation systems for Filamentous Fungi and an Overview of Fungal Gene structure. In: Leong, S. A., Berka R. M. (Editors) Molecular Industrial Mycology. Systems and Applications for Filamentous Fungi. Marcel Dekiker Inc. New York 1991. pp 1–29) and Turner G. 1994 (Vectors for genetic manipulation. In: Martinelli S. D., Kinghorn J. R.( Editors) Aspergillus: 50 years on. Progress in industrial microbiology vol 29. Elsevier Amsterdam 1994. pp. 641–666). The following commentary provides a summary of those teachings for producing transgenic Aspergillus according to the present invention.

In order to prepare the unnsgenic Aspergillus, expression constructs are prepared by inserting a heterologous nucleotide sequence (such as a nucleotide sequence coding for an amylase enzyme) into a construct designed for expression in filamentous fungi.

Several types of constructs used for heterologous expression have been developed. The constructs contain the promoter according to the present invention which is active in fungi. The heterologous nucleotide sequence can be fused to a signal sequence which directs the protein encoded by the heterolegous nucleotide sequence to be secreted. Usually a signal sequence of fungal origin is used. A terminator active in fungi may also be employed.

Another type of expression system has been developed in fungi where the heterologous nucleotide sequence is fused to a fungal gene encoding a stable protein. This can stabilise the protein encoded by the heterologous nucleotide sequence which encodes a desired polypeptide. In such a system a cleavage site, recognised by a specific protease, can be introduced between the fungal protein and the protein encoded by the heterologous nucleotide sequence, so the produced fusion protein can be cleaved at this position by the specific protease thus liberating the protein encoded by the heterologous nucleotide sequence. By way of example, one can introduce a site which is recognised by a KEX-2 like peptidase found in at least some Aspergilli (Broekhuijsen et al 1993 J Biotechnol 31 135–145). Such a fusion leads to cleavage in vivo resulting in protection of the expressed product and not a larger fusion protein.

Heterologous expression in Aspergillus has been reported for several genes coding for bacterial, fungal, vertebrate and plant proteins. With regard to product stability and host strain modifications, some heterologous proteins are not very stable when they are secreted into the culture fluid of fungi. Most fungi produce several extracellular proteases which degrade heterologous proteins. To avoid this problem special fungal strains with reduced protease production have been used as host for heterologous production.

For the transformation of filamentous fungi, several transformation protocols have been developed for many filamentous fungi (Ballance 1991, ibid). Many of them are based on preparation of protoplasts and introduction of DNA into the protoplasts using PEG and $Ca^{2+}$ ions. The transformed protoplasts then regenerate and the transformed fungi are selected using various selective markers. Among the markers used for transformation are a number of auxotrophic markers such as argB, trpC, niaD and pyrG, antibiotic resistance markers such as benomyl resistance, hygromycin resistance and phleomycin resistance. A commonly used transformation marker is the amdS gene of *A. nidulans* which in high copy number allows the fungus to grow with acrylamide as the sole nitrogen source.

Transcription of a DNA encoding peptidyl prolyl cis-trans isomerase by fungal organisms may be increased by inserting an enhancer sequence into the vector. Enhancers are relatively orientation and position independent.

An expression vector includes any vector capable of expressing peptidyl prolyl cis-trans isomerase encoding nucleic acids that are operatively linked with regulatory sequences, such as promoter regions, that are capable of expression of such DNAs. Thus, an expression vector refers to a recombinant DNA or RNA construct, such as a plasmid, a phage, recombinant virus or other vector, that upon introduction into an appropriate host cell, results in expression of the cloned DNA. Appropriate expression vectors are well known to those with ordinary skill in the art and include those that are replicable in eukaryotic and/or prokaryotic cells and those that remain episomal or those which integrate into the host cell genome.

Construction of vectors according to the invention employs conventional ligation techniques. Isolated plasmids or DNA fragments are cleaved, tailored, and religated in the form desired to generate the plasmids required. If desired, analysis to confirm correct sequences in the constructed plasmids is performed in a known fashion. Suitable methods for constructing expression vectors, preparing in vitro transcripts, introducing DNA into host cells, and performing analyses for assessing peptidyl prolyl cis-trans isomerase expression and function are known to those skilled in the art. Gene presence, amplification and/or expression may be measured in a sample directly, for example, by conventional Southern blotting, Northern blotting to quantitate the transcription of mRNA, dot blotting (DNA or RNA analysis), or in situ hybridisation, using an appropriately labelled probe which may be based on a sequence provided herein. Those skilled in the art will readily envisage how these methods may be modified, if desired.

The same or similar considerations will apply to the design of a vector encoding the desired polypeptide. Although it is not necessary, it is possible for the PPI and the desired polypeptide to be encoded on the same vector, whether episomal or integrating, and be expressed therefrom. Preferably, the desired polypeptide is a polypeptide encoded by a heterologous nucleotide sequence not derived from the host organism.

Typical examples of a nucleotide sequence encoding a desired polypeptide include sequences coding for proteins and enzymes that modify metabolic and catabolic processes. The heterologous nucleotide sequence may code for an agent for introducing or increasing pathogen resistance. The heterologous nucleotide sequence may code for a non-native protein of a filamentous fungus, preferably of the genus Aspergillus, or a compound that is of benefit to animals or humans. Examples of nucleotide sequences according to the invention include pectinases, pectin depolymerases, polygalacturonases, pectate lyases, pectin lyases, hexose oxidase, oxidoreductases, lipases, glucan lyase, rhamnogalacturonases, hemicellulases, endo-β-glucanases, arabinases, or acetyl esterases, or combinations thereof, as well as antisense sequences thereof. The desired polypeptide may be a protein giving nutritional value to a food or crop. Typical examples include plant proteins that can inhibit the formation of anti-nutritive factors and plant proteins that have a more desirable amino acid composition (e.g. a higher lysine content than a non-transgenic plant).

The desired polypeptide may be an enzyme that can be used in food processing such as chymosin, thaumatin and α-galactosidase. The desired polypeptide may moreover be any one of a pest toxin, ADP-glucose pyrophosphorylase (e.g. see EP-A-0455316), a glucanase or genomic β-1,4-endoglucanase.

The heterologous nucleotide sequence may code for an intron of a particular nucleotide sequence, wherein the intron can be in sense or antisense orientation.

The heterologous nucleotide sequence can be the nucleotide sequence coding for the arabinofuranosidase enzyme which is the subject of PCT patent application PCT/EP96/01009 (incorporated herein by reference). The heterologous nucleotide sequence can be any of the nucleotide sequences coding for the ADP-glucose pyrophosphorylase enzymes which are the subject of PCT patent application PCT/EP94/01082 (incorporated herein by reference). The heterologous nucleotide sequence can be any of the nucleotide sequences coding for the α-glucan lyase enzyme which are described in PCT patent application PCT/EP94103397 (incorporated herein by reference). The heterologous nucleotide sequence can be any of the sequences coding for *T. languinosus* amylase, as described in PCT patent application PCT/EP95/02607, incorporated herein by reference. The heterologous nucleotide sequence can be any of the nucleotide sequences coding for the glucanase enzyme which are described in PCT patent application PCT/EP96/01008 (incorporated herein by reference).

In a preferred aspect of the invention, the nucleic acid encoding PPI will also include, operatively linked thereto, an ER retention signal. Preferably, the ER retention signal is a tetrapeptide, which is advantageously HDEL (SEQ ID NO: 7), HEEL (SEQ ID NO: 8) or KDEL (SEQ ID NO: 9). The ER retention signal targets the polypeptide to the ER and causes it to be retained.

According to the second aspect of the present invention, there is provided a polypeptide which possesses a foldase activity and is characterised by having a capability to catalyse the cis-trans isomerisation of a peptide bond on the N terminal side of proline residues in polypeptides, having a signal sequence at the N terminus and an endoplasmic reticulum retention signal at the C terminus, and a molecular weight of 20.7 kilodaltons and a deduced isoelectric point of 6.27. Advantageously, the novel PPI according to this aspect of the invention is obtainable from a fungal organism, such as a filamentous fungus, for example those used in the biotechnology industry; preferably Aspergillus, Trichoderma or Penicillium; preferably *A. niger*.

An example of a PPI according to the invention is set forth in SEQ ID No. 2. The molecule identified in this sequence is obtainable from *Aspergillus niger* and is referred to herein as CYPB. PPI enzymes which satisfy the criteria set forth above are referred to herein in general as "CYPB" enzymes. In a preferred aspect, therefore, the invention provides CYPB as set forth in SEQ ID No. 2, or a bioisostere thereof.

As used herein, the term "bioisostere" is used in accordance with its common usage in the art, to refer to namely a compound having a similar (but not the same) or a different structure and having the same biological functional effect.

Advantageously, the bioisostere of the invention is obtainable from a fugal organism, such as a filamentous fungus, for example those used in the biotechnology industry; preferably Aspergillus, Trichoderma or Penicillium preferably *A. niger*.

According to a further aspect of the present invention, there is provided a nucleic acid encoding an enzyme according to the invention. In addition to being useful for the production of recombinant PPI protein, these nucleic acids are also useful as probes, thus readily enabling those skilled in the art to identify and/or isolate nucleic acid encoding PPIs or homologues thereof. The nucleic acid may be unlabelled or labelled with a detectable moiety. Furthermore, nucleic acid according to the invention is useful e.g. in a method determining the presence of PPI-specific nucleic acid, said method comprising hybridising the DNA (or RNA) encoding (or complementary to) PPI to a test sample nucleic acid and determining the presence of the PPI. In another aspect, the invention provides nucleic acid sequence that is complementary to, or hybridises under stringent conditions to, a nucleic acid sequence encoding a PPI of a fragment thereof.

Advantageously, fragments of PPI-encoding nucleic acids are between 10 and 200 nucleotides in length, preferably between 15 and 50 nucleotides in length, and most preferably about 20 nucleotides in length.

The invention also provides a method for amplifying a nucleic acid test sample comprising priming a nucleic acid polymerase (chain) reaction with nucleic acid (DNA or RNA) encoding (or complementary to) the PPI.

In still another aspect of the invention, the nucleic acid is DNA and further comprises a replicable vector comprising the nucleic acid encoding the PPI operably linked to control sequences recognised by a host transformed by the vector. Furthermore the invention provides host cells transformed with such a vector and a method of using a nucleic acid encoding a PPI to effect the production of PPI, comprising expressing PPI-encoding nucleic acid in a culture of the transformed host cells and, if desired, recovering PPI from the host cell culture.

Furthermore, the present invention relates to isolated PPI proteins and bioisosteres thereof encoded by the above-described nucleic acids.

Isolated PPI nucleic acid includes nucleic acid that is free from at least one contaminant nucleic acid with which it is ordinarily associated in the natural source of PPI nucleic acid or in crude nucleic acid preparations, such as DNA libraries and the like. Isolated nucleic acid thus is present in other than in the form or setting in which it is found in nature. However, isolated PPI encoding nucleic acid includes PPI nucleic acid in ordinarily PPI-expressing cells where the nucleic acid is in a chromosomal location different from that of natural cells or is otherwise flanked by a different DNA sequence than that found in nature.

In accordance with the present invention, there are provided isolated nucleic acids, e.g. DNAs or RNAs, encoding CYPB having the sequence set forth in SEQ. ID. No. 2, or fragments thereof. In particular, the invention provides a DNA molecule encoding CYPB as set forth in SEQ. ID. No. 2, or a fragment thereof. By definition, such a DNA comprises a coding single stranded DNA, a double stranded DNA of said coding DNA and complementary DNA thereto, or this complementary (single stranded) DNA itself.

The preferred sequence encoding CYPB is that having substantially the same nucleotide sequence as the coding sequences in SEQ ID No. 2, with the nucleic acid having the same sequence as the coding sequence in SEQ ID No. 2 being most preferred. As used herein, nucleotide sequences which are substantially the same share at least about 90% identity.

The nucleic acids of the invention, whether used as probes or otherwise, are preferably substantially homologous to the sequence of CYPB as shown in SEQ ID No. 2. "Substantial homology", where homology indicates sequence identity, means more than 40% sequence identity, preferably more than 45% sequence identity and most preferably a sequence identity of 50% or more, as judged by direct sequence alignment and comparison.

Substantially homologous amino acid sequences and nucleotide sequences can have greater than 75% homology (e.g., at least 80% homology, or at least 85% homology, such as at least 90% homology, or even at least 95% homology, for instance at least 97% homology). Nucleotide sequence homology can be determined using the "Align" program of Myers and Miller, ("Optimal Alignments in Linear Space", CABIOS 4, 11–17, 1988, incorporated herein by reference) and available at NCBI. Alternatively or additionally, the term "homology", for instance, with respect to a nucleotide or amino acid sequence, can indicate a quantitative measure of homology between two sequences. The percent sequence homology can be calculated as $(N_{ref}-N_{dif})*100/N_{ref}$, wherein $N_{dif}$ is the total number of non-identical residues in the two sequences when aligned and wherein $N_{ref}$ is the number of residues in one of the sequences. Hence, the DNA sequence AGTCAGTC will have a sequence similarity of 75% with the sequence AATCAATC ($N_{ref}=8$; $N_{dif}=2$). Alternatively or additionally, "homology" with respect to sequences can refer to the number of positions with identical nucleotides or amino acids divided by the number of nucleotides or amino acids in the shorter of the two sequences wherein alignment of the two sequences can be determined in accordance with the Wilbur and Lipman algorithm (Wilbur and Lipman, 1983 PNAS USA 80:726, incorporated herein by reference), for instance, using a window size of 20 nucleotides, a word length of 4 nucleotides, and a gap penalty of 4, and computer-assisted analysis and interpretation of the sequence data including alignment can be conveniently performed using commercially available programs (e.g., Intelligenetics™ Suite, Intelligenetics Inc. Calif.). When RNA sequences are said to be similar, or have a degree of sequence identity or homology with DNA sequences, thymidine (T) in the DNA sequence is considered equal to uracil (U) in the RNA sequence.

RNA sequences within the scope of the invention can be derived from DNA sequences, by thymidine (T) in the DNA sequence being considered equal to uracil (U) in RNA sequences.

Additionally or alternatively, amino acid sequence similarity or identity or homology can be determined using the BlastP program (Altschul et al., Nucl. Acids Res. 25, 3389–3402, incorporated herein by reference) and available at NCBI, advantageously using default parameters. The following references (each incorporated herein by reference) provide algoriths for comparing the relative identity or homology of amino acid residues of two proteins, and additionally or alternatively with respect to the foregoing, the teachings in these references can be used for determining percent homology or identity: Needleman S B and Wunsch C D, "A general method applicable to the search for similarities in the amino acid sequences of two proteins," *J. Mol. Biol.* 48:444–453 (1970); Smith T F and Waterman M S, "Comparison of Bio-sequences," *Advances in Applied Mathematics* 2:482489 (1981); Smith T F, Waterman M S and Sadler J R, "Statistical characterization of nucleic acid sequence functional domains," *Nucleic Acids Res.,* 11:2205–2220 (1983); Feng D F and Dolittle R F, "Progressive sequence alignment as a prerequisite to correct phylogenetic trees," *J. of Molec. Evol.,* 25:351–360 (1987); Higgins D G and Sharp P M, "Fast and sensitive multiple sequence alignment on a microcomputer," *CABIOS,* 5: 151–153 (1989); Thompson J D, Higgins D G and Gibson T J, "ClusterW: improving the sensitivity of progressive multiple sequence alignment through sequence weighing, positions-specific gap penalties and weight matrix choice, *Nucleic Acid Res.,* 22:4673–480 (1994); and, Devereux J, Haeberlie P and Smithies O, "A comprehensive set of sequence analysis program for the VAX," *Nucl Acids Res.,* 12: 387–395 (1984).

Preferably, nucleic acids according to the invention are fragments of the CYPB-encoding sequence. Fragments of the nucleic acid sequence of a few nucleotides in length, preferably 5 to 150 nucleotides in length, are especially useful as probes.

Exemplary nucleic acids can alternatively be characterised as those nucleotide sequences which encode a CYPE protein and hybridise to the DNA sequences set forth SEQ ID No. 2, or a selected fragment of said DNA sequence. Preferred are such sequences encoding CYPB which hybridise under high stringency conditions to the sequence of SEQ ID No. 2 or a fragment thereof as defined above.

Stringency of hybridisation refers to conditions under which polynucleic acids hybrids are stable. Such conditions are evident to those of ordinary skill in the field. As known to those of skill in the art, the stability of hybrids is reflected in the melting temperature (Tm) of the hybrid which decreases approximately 1 to 1.5° C. with every 1% decrease in sequence homology. In general, the stability of a hybrid is a function of sodium ion concentration and temperature. Typically, the hybridisation reaction is performed under conditions of higher stringency, followed by washes of varying stringency.

As used herein, high stringency refers to conditions that permit hybridisation of only those nucleic acid sequences that form stable hybrids in 1 M Na$^+$ or an equivalent salt concentration, at 65–68° C. High stringency conditions can be provided, for example, by hybridisation in an aqueous solution containing 6×SSC, 5×Denhardt's, 1% SDS (sodium dodecyl sulphate), 0.1 Na$^+$ pyrophosphate and 0.1 mg/ml denatured salmon sperm DNA as non specific competitor. Following hybridisation, high stringency washing may be done in several steps, with a final wash (about 30 min) at the hybridisation temperature in 0.2–0.1×SSC, 0.1% SDS.

Moderate stringency refers to conditions equivalent to hybridisation in the above described solution but at about 60–62° C. In that case the final wash is performed at the hybridisation temperature in 1×SSC, 0.1% SDS.

Low stringency refers to conditions equivalent to hybridisation in the above described solution at about 52–56° C. In that case, the final wash is performed at the hybridisation temperature in 4×SSC, 0.1% SDS.

It is understood that these conditions may be adapted and duplicated using a variety of buffers, e.g. formamide-based buffers, and temperatures. Denhardt's solution and SSC are well known to those of skill in the art as are other suitable hybridisation buffers (see, e.g. Sambrook, et al., eds. (1989) Molecular Cloning: A Laboratory Manual, Cold Spring Harbor Laboratory Press, New York or Ausubel, et al., eds. (1990) Current Protocols in Molecular Biology, John Wiley & Sons, Inc.). Optimal hybridisation conditions have to be determined empirically, as the length and the GC content of the probe also play a role.

The CYPB protein of the present invention comprises an ER retention signal. In a preferred aspect of the present invention, accordingly, there is provided a polypeptide possessing foldase activity characterised by having a capability to catalyse the cis-trans isomerisation of a peptide bond on the N terminal side of proline residues in polypeptides, encoded by a nucleic acid capable of hybridising under conditions of low, medium or high stringency with a 17 base oligonucleotide derived from SEQ ID No. 1. Preferably, low stringency conditions are used.

SEQ. ID. No. 1 represents a degenerated sequence encoding an ER retention signal. Since this signal is likely to be located on any CYPB protein which is located in the ER, the presence of this sequence may advantageously be used to characterise and isolate CYPB polypeptides in accordance with the present invention.

Given the guidance provided herein, the nucleic acids of the invention are obtainable according to methods well known in the art. For example, a DNA of the invention is obtainable by chemical synthesis, using polymerase chain reaction (PCR) or by screening a genomic library or a suitable cDNA library prepared from a source believed to possess CYPB and to express it at a detectable level.

Chemical methods for synthesis of a nucleic acid of interest are known in the art and include triester, phosphite, phosphoramidite and H-phosphonate methods, PCR and other autoprimer methods as well as oligonucleotide synthesis on solid supports. These methods may be used if the entire nucleic acid sequence of the nucleic acid is known, or the sequence of the nucleic acid complementary to the coding strand is available. Alternatively, if the target amino acid sequence is known, one may infer potential nucleic acid sequences using known and preferred coding residues for each amino acid residue.

An alternative means to isolate a gene encoding a PPI according to the invention is to use PCR technology as described e.g. in section 14 of Sambrook et al., 1989. This method requires the use of oligonucleotide probes that will hybridise to PPI nucleic acid. Strategies for selection of oligonucleotides are described below.

Libraries are screened with probes or analytical tools designed to identify the gene of interest or the protein encoded by it. For cDNA expression libraries suitable means include monoclonal or polyclonal antibodies that recognise and specifically bind to CYPB; oligonucleotides of about 20 to 80 bases in length that encode known or suspected CYPB cDNA from the same or different species; and/or complementary or homologous cDNAs or fragments thereof that encode the same or a hybridising gene. Appropriate probes for screening genomic DNA libraries include, but are not limited to oligonucleotides, cDNAs or fragments thereof that encode the same or hybridising DNA; and/or homologous genomic DNAs or fragments thereof.

A nucleic acid encoding CYPB may be isolated by screening suitable cDNA or genomic libraries under suitable hybridisation conditions with a probe, i.e. a nucleic acid disclosed herein including oligonucleotides derivable from the sequences set forth in SEQ ID NO. 2. Suitable libraries are commercially available or can be prepared e.g. from cell lines, tissue samples, and the like.

As used herein, a probe is e.g. a single-stranded DNA or RNA that has a sequence of nucleotides that includes between 10 and 50, preferably between 15 and 30 and most preferably at least about 20 contiguous bases that are the same as (or the complement of) an equivalent or greater number of contiguous bases set forth in SEQ ID No. 2. The nucleic acid sequences selected as probes should be of sufficient length and sufficiently unambiguous so that false positive results are minimised. The nucleotide sequences are usually based on conserved or highly homologous nucleotide sequences or regions of CYPB. The nucleic acids used as probes may be degenerate at one or more positions. The use of degenerate oligonucleotides may be of particular importance where a library is screened from a species in which preferential codon usage in that species is not known.

Preferred regions from which to construct probes include 5' and/or 3' coding sequences, sequences predicted to encode ligand binding sites, and the like. For example, either the full-length cDNA clone disclosed herein or fragments thereof can be used as probes. Preferably, nucleic acid probes of the invention are labelled with suitable label means for ready detection upon hybridisation. For example, a suitable label means is a radiolabel. The preferred method of labelling a DNA fragment is by incorporating $\alpha^{32}$P dATP with the Klenow fragment of DNA polymerase in a random priming reaction, as is well known in the art. Oligonucleotides are usually end-labelled with $\gamma^{32}$P-labelled ATP and polynucleotide kinase. However, other methods (e.g. non-radioactive) may also be used to label the fragment or oligonucleotide, including e.g. enzyme labelling, fluorescent labelling with suitable fluorophores and biotinylation.

After screening the library, e.g. with a portion of DNA including substantially the entire CYPB-encoding sequence or a suitable oligonucleotide based on a portion of said DNA, positive clones are identified by detecting a hybridisation signal; the identified clones are characterised by restriction enzyme mapping and/or DNA sequence analysis, and then examined, e.g. by comparison with the sequences set forth herein, to ascertain whether they include DNA encoding a complete CYPB (i.e., if they include translation initiation and termination codons). If the selected clones are incomplete, they may be used to rescreen the same or a different library to obtain overlapping clones. If the library is genomic, then the overlapping clones may include exons and introns. If the library is a cDNA library, then the overlapping clones will include an open reading frame. In both instances, complete clones may be identified by comparison with the DNAs and deduced amino acid sequences provided herein.

In order to detect any abnormality of endogenous CYPB, genetic screening may be carried out using the nucleotide sequences of the invention as hybridisation probes. Also, based on the nucleic acid sequences provided herein antisense-type agents to reduce expression of CYPB, if desired, may be designed.

It is envisaged that the nucleic acid of the invention can be readily modified by nucleotide substitution, nucleotide deletion, nucleotide insertion or inversion of a nucleotide stretch, and any combination thereof. Such mutants can be used e.g. to produce a CYPB mutant that has an amino acid sequence differing from the CYPB sequences as found in nature. Mutagenesis may be predetermined (site-specific) or random. A mutation which is not a silent mutation must not place sequences out of reading frames and preferably will not create complementary regions that could hybridise to produce secondary mRNA structure such as loops or hairpins.

The invention is described below, for the purposes of illustration only, in the following examples:

EXAMPLE 1

Construction of an *Aspergillus niger* cDNA Library

λZAP-*A.niger*N402 cDNA library is constructed from *A. niger* cDNA by use of ZAP-cDNA synthesis kit from Stratagene, using the instructions provided by the manufacturer.

EXAMPLE 2

Screening of the *Aspergillus niger* cDNA Library

Approximately 2×50.000 pfu are plated on large (22×22 cm) NZY plates containing the following medium (per liter): 5 g NaCl, 2 g MgSO$_4$.7H$_2$O, 5 g yeast extract, 10 g casein hydrolysate, 15 g agar, pH adjusted to 7.5 with NaOH. The medium is autoclaved, cooled to about 65° C. and poured into the plates. 240 ml of medium is used per plate.

The inoculated NZY plates are incubated overnight at 37° C. and plaque lifts of the plates are made. Two lifts are made for each plate on Hybond N (Amersham) filters. The DNA is fixed using UV radiation for 4 min. and the filters are hybridised as described in the following using, as the probe, a degenerate oligonucleotide that is labelled with $^{32}$P-DCTP using Terminal Transferase (Boehringer Mannheim) according the following procedure.

500 pmol of the degenerate oligo nucleotide is used. After 3 min. incubation at 94° C. in a Terminal Transferase reaction buffer (Boehringer Mannheim), the mixture is chilled on ice and 4 µl $^{32}$P-dCTP is added. The labelling reaction is started by addition of 10 units Terminal Transferase (Boehringer Mannheim). After incubation at 37° C. for 30 min., the enzyme is heat inactivated by a 5 min. incubation at 70° C. The radio-labelled oligo nucleotide is purified on a NAP 5 column (Pharmacia—containing Sephadex G-25 medium).

The filters are prehybridised for 4 hours at 56° C. in 50 ml prehybridisation buffer containing 12.5 ml 20×SSC (0.3 M Na$_3$citrate, 3 M NaCl), 2.5 ml 100×Denhardt's solution, 2.5 ml 10% SDS and 32.5 ml water. 300 µl 10 mg/ml denatured salmon sperm DNA is added to the prehybridisation buffer immediately before use. Following prehybridisation, the radiolabelled oligonucleotide is added and filters are hybridised overnight at 56° C. Next day the filters are washed twice with 4×SSC+0.1% SDS for 30 min at 56° C.

The filters are autoradiographed for 16 hours and positive clones are isolated. A clone is counted as positive only if there is a hybridisation signal on both plaque lifts of the NZY plate.

Six putative clones are isolated and are purified by plating on small Petri dishes, after which they are subjected to a second screening, essentially as described above. Four clones are eventually selected for the conversion to plasmids using the Rapid Excision Kit (Stratagene).

Sequencing of the obtained plasmids is done with the Reverse and Universal sequence primers. The plasmid containing the cypB gene encoding a cyclophilin like peptidyl prolyl cis-trans isomerase B is designated pPD23.

EXAMPLE 3

Characterisation of the pPD23 Plasmid Containing the cypB Gene

A restriction map of the clone is made. The fragment is cloned in the EcoRI and XhoI site of pBluescript SK+. The restriction map showing the structure op pPD23 is shown in FIG. 1. The gene is sequenced using the cycle sequencing method. The complete sequence is shown in SEQ. ID. No. 2. The sequence is determined on both strands for the whole construct.

The deduced amino acid sequence is aligned using the ClustalW program with three cyclophilin like peptidyl prolyl cis-trans isomerases B. The alignment is shown in FIG. 2.

The above alignment shows that CYPB is homologous to the other known CYPB sequences.

A search in the SWISS-PROT database is performed and does not show any sequences with a higher homology than those shown in the alignment (FIG. 2). The sequence with the highest homology is a precursor for the cyclophilin like peptidyl prolyl cis-trans isomerase from Orpinimyces sp. where the identity is found to be 63% (FIG. 3).

Residues 1–23 are recognised as a signal sequence, leaving a mature protein of 186 amino acids with a deduced molecular weight of 20,7 kDa and a deduced isoelectric point (pI) of 6.27. The CYPB protein contains a putative E.R. retention signal at its extreme C-terminus (position 209–212). One putative N-glycosylation site is found in CYPB at position 139–142. A conserved motif for cyclophilin-type peptidyl-prolyl cis-trans isomerase is present at position 79–96.

EXAMPLE 4

Expression of cypB in *E. coli*

A fragment, containing the part of the gene encoding for the mature CYPB protein, is generated by PCR with the following primers:
upper primer:
5' ccc ata tgg aag atg ctc age ccc ggg gcc cca aga 3' (SEQ. ID. No. 3)
lower primer:

5' cga agc tta gtg gtg gtg gtg gtg gtg gct gct acc ttt ttc t 3' (SEQ. ID. No. 4)

PCR is performed at 52° C. using pfu polymerase. The E.R. target sequence is excluded from this construct. Furthermore, the C-terminal part of the protein is extended with a HIS-tag. This fragment is subsequently cloned in plasmid pET-24a (+) (Novagen), allowing expression of the gene in *E. coli*. This construct is transformed to *E. coli* strain BL21(DE3)pLysS. Expression of cypB is induced with 1 mM IPTG which is added to the culture at $OD_{600}=1$.

*E. coli* expressed protein is purified by means of Immobilised Metal Affinity Chromatography (Ni-NTA resin, Qiagen) and gel filtration (Superdex 75, Pharmacia). The apparent molecular weight of the purified CYPB is determined on a SDS-PAGE gel to be approximately 21 kDa. The exact molecular mass is determined by MALDI-TOF analysis, revealing a molecular weight of 21100.6 Da. N-terminal sequencing revealed the first 10 amino acids of the mature sequence (EDAQPRGPK—residues 24 to 32 in SEQ. ID. No. 2).

A assay based on the stereospecific degradation of the substrate suc-Ala-Ala-Pro-Phe-pNA (Sigma) by α-chemotrypsin (Boehringer Mannheim) is set up to determine the activity of CYPB. The trans-isomer of this substrate is rapidly degraded by α-chemotrypsin. In water, 88% of the substrate is present as trans and 12% as cis-isomer. The conversion of the cis-isomer to the trans-isomer is rate limiting and is catalysed by peptidyl prolyl cis-trans isomerases.

CYPB is assayed at 25° C. in 50 mM HEPES buffer pH 7.8 containing 50 μM substrate and 25 μM α-chemotrypsin. 0.5 nM CYPB protein is added to the mixture and the absorbance at 380 nm is measured every 0.5 sec. Addition of CYPB protein clearly leads to a quicker degradation of the substrate, proving the foldase activity thereof.

EXAMPLE 5

Co-expression of CYPB and a Triacylglycerol Lipase

Lipase-expressing and CypB Plasmids

Figure 4:
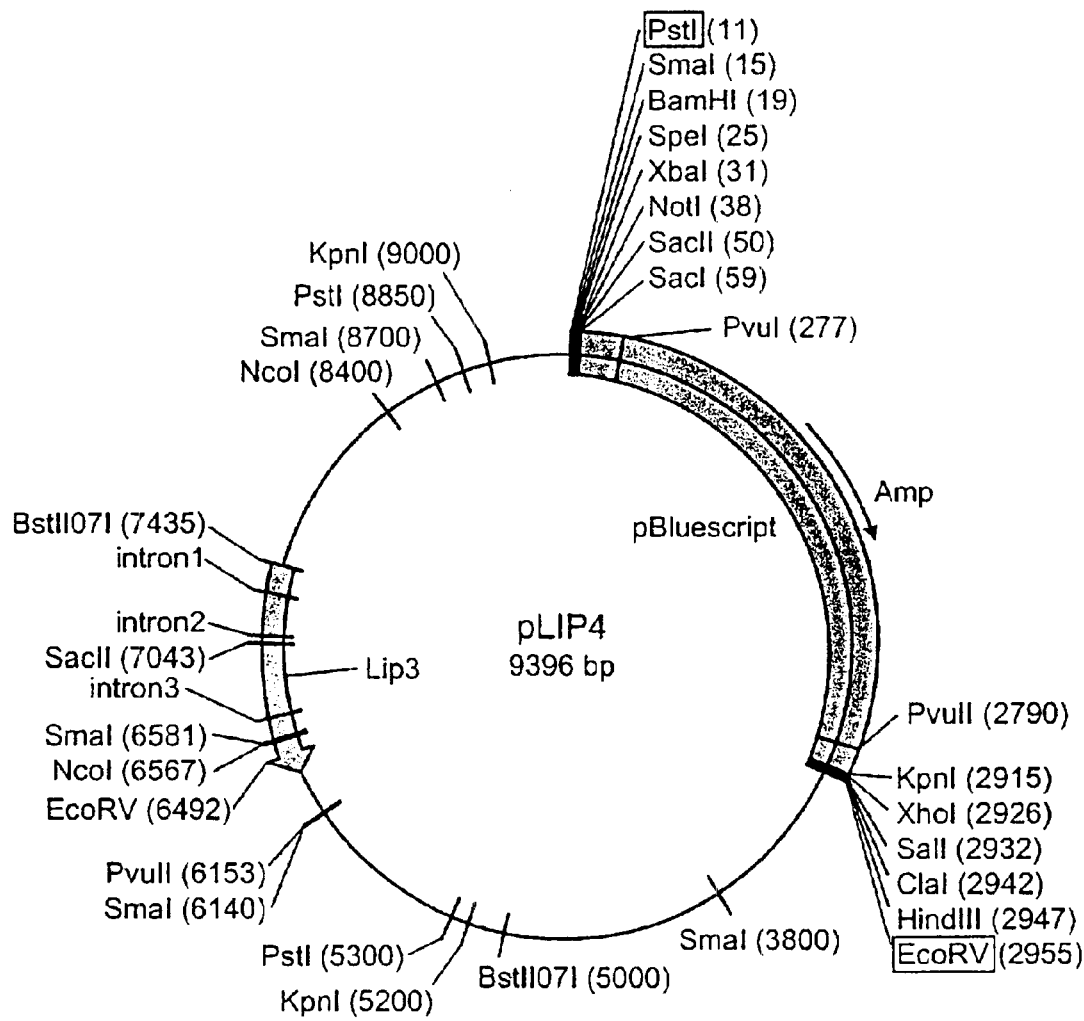
FIG. 4 is a representation of pLIP4, which encodes the lipA gene.
Figure 5:
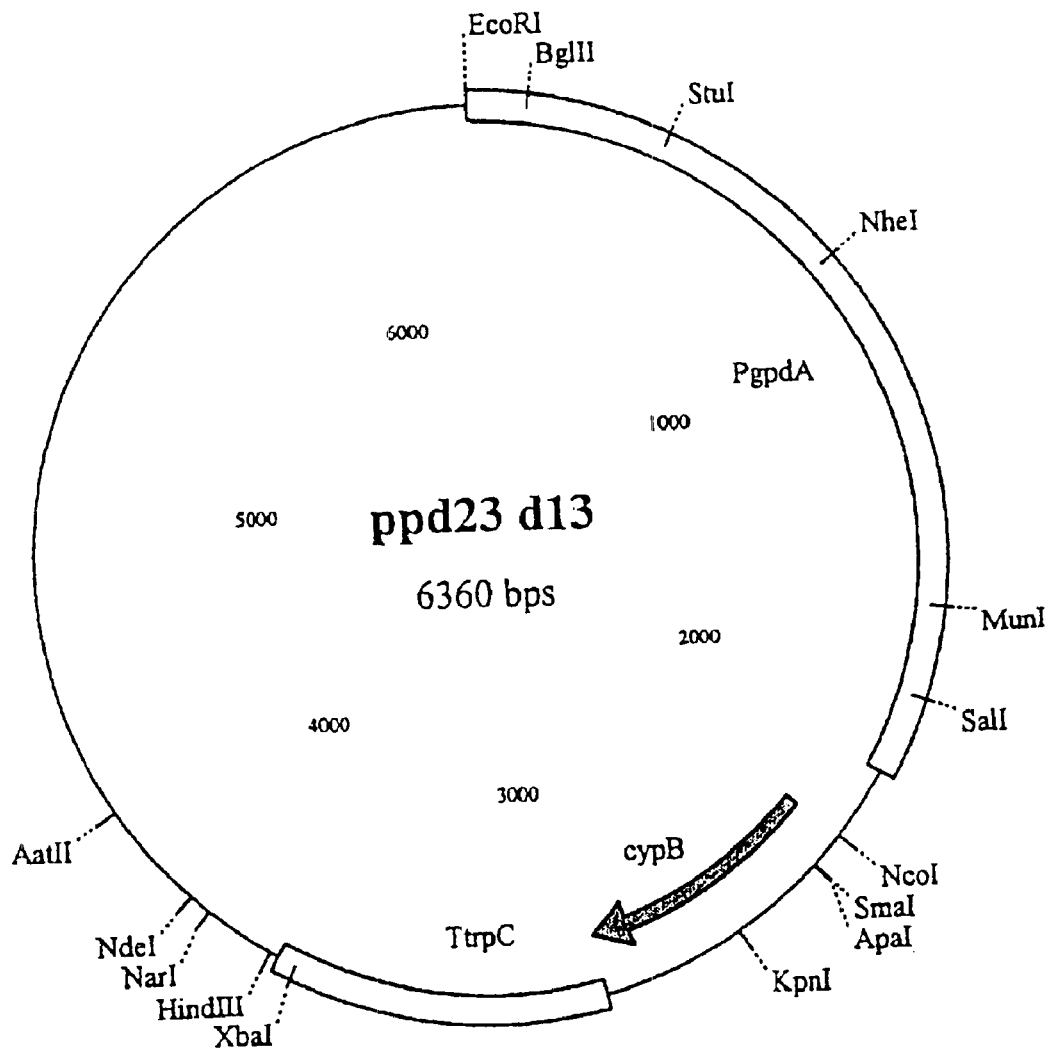
FIG. 5 is a representation of ppd23d13.
Figure 6:
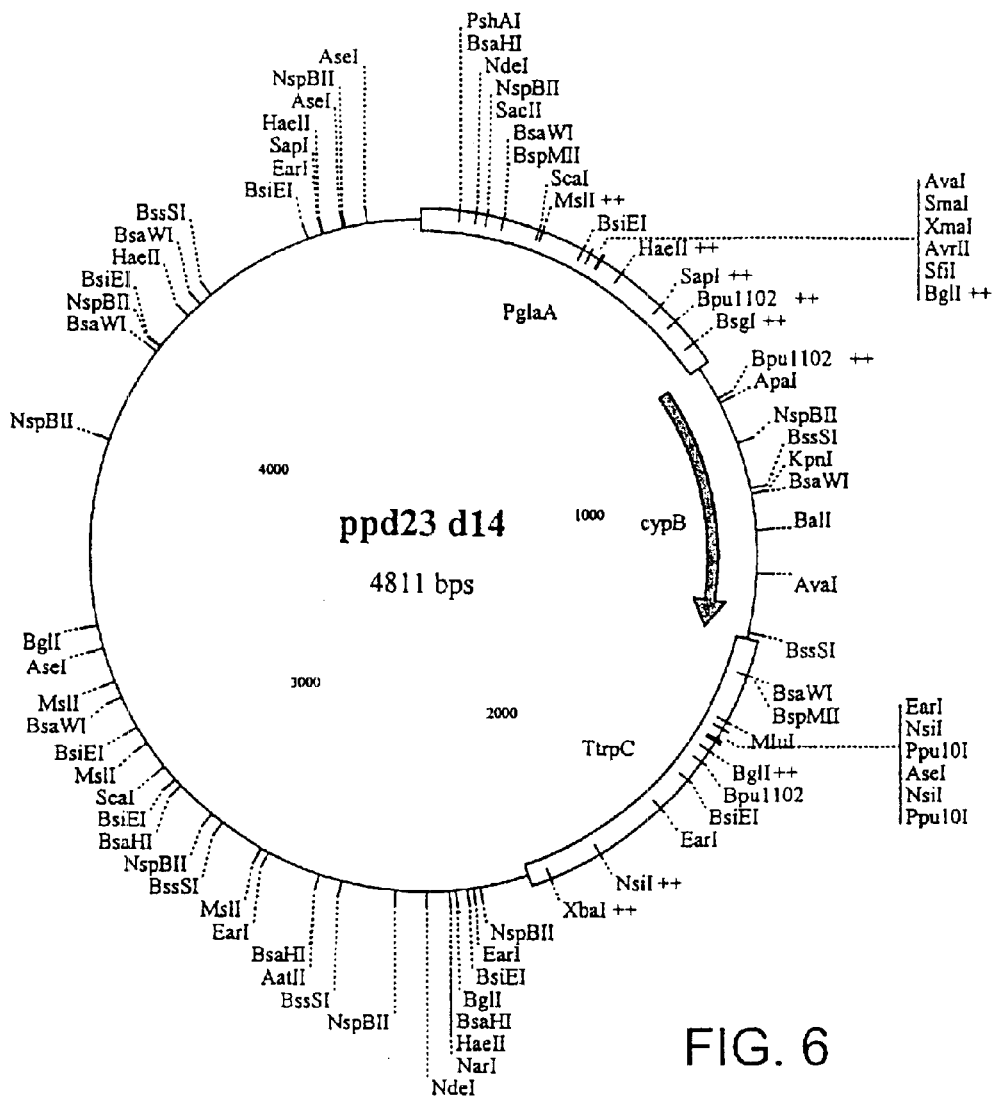
FIG. 6 is a representation of ppd23d14.

The plasmid pLIP4 (FIG. 4) comprises the entire genomic sequence of the lipA gene. This sequence is set forth in SEQ ID NO: 6. CYPB is expressed from either ppd23d14 or ppd23d13, as shown in FIGS. 5 and 6 respectively. Ppd23d14 comprises the CypB sequence under the control of the glaA promoter (generally available; see, for example, Ward et al., (1995) Biotechnology 13: 498–503), which is inducible. Ppd23d13 comprises the CypB sequence under the control of the *A. nidulans* gpdA promoter (Punt et al., (1991) J. Biotechnol. 17: 19–34), which is constitutively active. In both cases, the CypB gene is followed by the *A. nidulans* trpC terminator.

Antibiotic resistance is incorporated into the plasmids by insertion of a hygromycin resistance gene (isolated from *Streptomyces hygroscopicus* and *E. coli*) under the control of the gpdA promoter.

Transformation of the *Aspergillus tubigensis* Strain 3M pyrA with the Lipase Gene Spores from the *A. tubigensis* strain 3M pyr A are cultivated overnight at 34° C. in a shake flask containing minimal medium supplemented with 2% glucose and 10 mM uridine. The mycelium is harvested and resuspended in lysis buffer plus lysing enzyme. The protoplasts produced are mixed with pLIP4, together with ppd23d14 or ppd23d13, by cotransformation, using pyrG and antibiotic resistance markers to select for the desired recombinants.

In Situ Detection of Lipase Production In Transformed Aspergillus Strains

A screening procedure used to visualise fungal lipase after ultrathin layer isoelectric focusing is adapted to screen Aspergillus transformants grown on agar plates. This procedure is very convenient for the initial analysis of expressing and non-expressing transformed Aspergillus strains. Screening of lipase producers on agar plates is done using 2% olive oil as the substrate of the enzyme (lipase) as well as the inducer of the lipase promoter. In addition, the plate contains a fluorescent dye Rhodamine B (N-9-(2-carboxyphenyl)-6-(diethylamino)-3H-xanthen-3-ylidene-N-ethylethanaminium chloride). In the presence of olive oil, the transformants are induced to secrete lipase. The lipase secreted into the agar plate hydrolyses the olive oil causing the formation of orange fluorescent colonies that are visible upon UV irradiation (350 nm). The detection of fluorescent colonies is observed after about 24 hours of growth, depending on the transformant. After several days of growth, the lipase producing strains can be identified as orange fluorescent strains that are visible by eye. Under these plate screening conditions, the untransformed strain give no background fluorescence and appear as opaque pink colonies. However, one should be conscious of possible contaminating yeast and bacterial strains that can grow rapidly on the oil containing plates. Contamination is prevented by the incorporation of antibiotics—Ampicillin.

Characterisation of Lipase Secreting Transformants

The 16 transformants that show orange fluorescent halos are cultivated in shake flasks containing 100 ml of minimal medium plus 1% olive oil, 0.5% yeast extract, 0.2% casamino acids and grown for 8 days. The amount of lipase secreted is quantitated by applying 10 μl of cell-free culture supernatant into holes punched in the olive oil—rhodamine B agar plates and incubating the plates overnight at 37° C. Using this technique, the cell free culture supernatant from the 5 transformants that give the most intense fluorescence are further analysed by chromatography.

Purification of Recombinant Lipase by Hydrophobic Interaction Chromatography (HIC)

Culture supernatant from the five different lipase secreting transformants found positive by the plate screening method are desalted using NAP 5 columns (Pharmacia: contain Sephadex G 25 medium) and equilibrated in 1M $(NH_4)_2SO_4$, 50 mM sodium acetate pH 5.5. The desalted culture supernatant is fractionated by hydrophobic interaction chromatography on a Biogel Phenyl-5 PW Column (Biorad). Elution is done by a descending salt gradient of 1M to zero Molar $(NH_4)_2SO_4$, 20 mM sodium acetate, pH 5.5. A single discrete protein peak is observed after fractionation. The area of the protein peaks is calculated among the different transformants and compared with the untransformed strains. The table below summarises the levels of Lipase secreted by the 5 transformants. The best transformant shows a 62 fold increased in the amount of lipase purified after HIC fractionation. The table also shows the varying amounts of lipase produced by the different transformants after 6 days of growth under unoptimised small scale shake flask condition.

| Transformants grown for 6 days in 1% olive oil as the carbon source | Levels of Secreted Lipase after HIC = Area of the discrete protein peak/area of 6M) Area = height × FWHM (full width half median) |
|---|---|
| L43-6 Flipper | 61.9 |
| L3-6 | 10.5 |
| L1-6 | 13.1 |
| L13-6 | 17.0 |
| L47-6 | 29.3 |
| 6M-6 Untransformed 6M strain | 1.0 | b. Characterisation of Recombinant Lipase

1. Amino Acid Analysis And Protein Determination

The discrete protein peak after fractionation by HIC is freeze dried and resuspended in water. The amino acid composition and the protein concentration of the purified lipase protein are determined to obtain a correlation coefficient between UV absorbance at 280 nm and protein concentration. This allows the estimation of Lipase concentration in homogenous preparations.

The Lipase protein is carboxymethylated and the sequence of the first 15 amino acids is determined by N-terminal amino acid sequencing. The 15 amino acid sequence of the recombinant lipase is exactly the same as the native lipase indicating correct signal sequence cleavage.

2. SDS-PAGE Electrophoresis

The different protein fractions collected after HIC are separated on a 12% Tris-Glycine SDS gel. Silver staining reveals one protein band, confirming the homogeneity of the protein peaks. In addition, the crude extract shows a major lipase band as the only protein band that accumulated in the culture supernatant in very high amounts when the fungus is cultured in medium containing oil.

3. Detection of the Presence of a Covalently Attached N-linked Oligosaccharides in Recombinant Lipase The detection of N-linked oligosaccharides is achieved by digestion of the lipase with Endo- -N-acetyl-glucosamidase H from Streptomyces (Sigma). Endo H treatment of recombinant lipase secreted into the growth medium alters the mobility of the band seen on SDS-PAGE and runs as a single species with a molecular mass of approximately 30 kDa. This indicates the extent of N-linked glycosylation.

4. Matrix Assisted Laser Desorption Mass Spectrometry Recombinant Lipase

MALDI-TOF mass spectrometry is performed using purified lipase mixed with a matrix solution consisting of sinapinic acid (3,5-Dimethoxy-4-hydroxy cinnamic acid) in 70% acetonitrile, 0.1% TFA. The molecular mass determined from the desalted recombinant lipase is 32,237 Daltons. Deglycosylated lipase generated by digestion with endoglycosidase H and analysed directly by Maldi-MS gave an estimate of the molecular weight of the polypeptide backbone of 29.325 Da.

Using this analysis, the presence and the approximate number of N-inked oligosaccharides on the glycoprotein can be determined. In conclusion, N-linked oligosaccharides account for approximately 10% of the molecular weight of recombinant lipase.

| Mass Spectrometry analysis of LIPASE | | |
|---|---|---|
| | | + endoglycosidase H |
| recombinant lipase | 32,237 daltons | 29,326 daltons |
| native lipase | 30,310 daltons | 29,333 daltons |

EXAMPLE 6

Overexpression of cvpB in *Aspergillus niger*

Aspergillus strain N592 (cspA1, pyrA5) has been transformed with a plasmid allowing expression of cypB under the strong constitutive gpdA promoter. Putative transformants are screened by PCR to confirm the presence of this plasmid. The number of integrated copies and the level of cypB expression in this strain (N592::pPD23d13) is determined by Southern and Northern analysis respectively.

The Southern analysis shows clearly that strain N592::pPD23d13 contains multiple copies of the integrated plasmid pPD23d13. The level of expression of cypB in this strain is approximately 15 times higher than the wild type expression level.

To determine whether this strain is capable of secreting more protein, a growth experiment is set up in which the wild type strain (N402) and N592::pPD23d13 are grown in the presence of 2% (w/v) starch. Starch is known to be a specific inducer for the expression of glucoamylase. Supernatant samples were therefor assayed for glucoamylase activity and amounts of secreted proteins.

Glucoamylase is regarded as a well secreted protein and it is commonly used as a fusion protein to aid the secretion of difficult target proteins.

The overexpression of cypB clearly leads to an increased production level of glucoamylase. An almost two fold increase of glucoamylase activity is measured after 72 hours of induction. No de novo glucoamylase production is seen at this time, most likely because of a depletion of the inducing carbon source.

EXAMPLE 7

Localisation of CYPB

Secretion of proteins from eukaryotic cells is a complex process. Newly synthesised secretory and membrane proteins enter the endoplasmic reticulum (ER) in an unfolded state and must acquire a specific conformation before they can be transported further within the secretory pathway. A number of proteins have been found within the lumen of the ER. These include BiP (binding protein, a homologue of the 70 kDa heat-shock protein), protein disulphide isomerase (PDI) and peptidyl prolyl cis-trans isomerase (PPI). These foldases are involved in catalysing the folding of a protein from the unfolded to the native state. In order to remain in the ER, and therefor to be diverted from the bulk flow of secreted proteins, foldases have specific retention and retrieval signal. A common carboxy terminal tetrapeptide, HDEL has been identified as a signal capable of retaining a protein within the lumen of the ER. Removal of this tetrapeptide leads to secretion of the protein (Pelham (1990) Trends Biochem. Sci. 15, 483–486)

Figure 7:
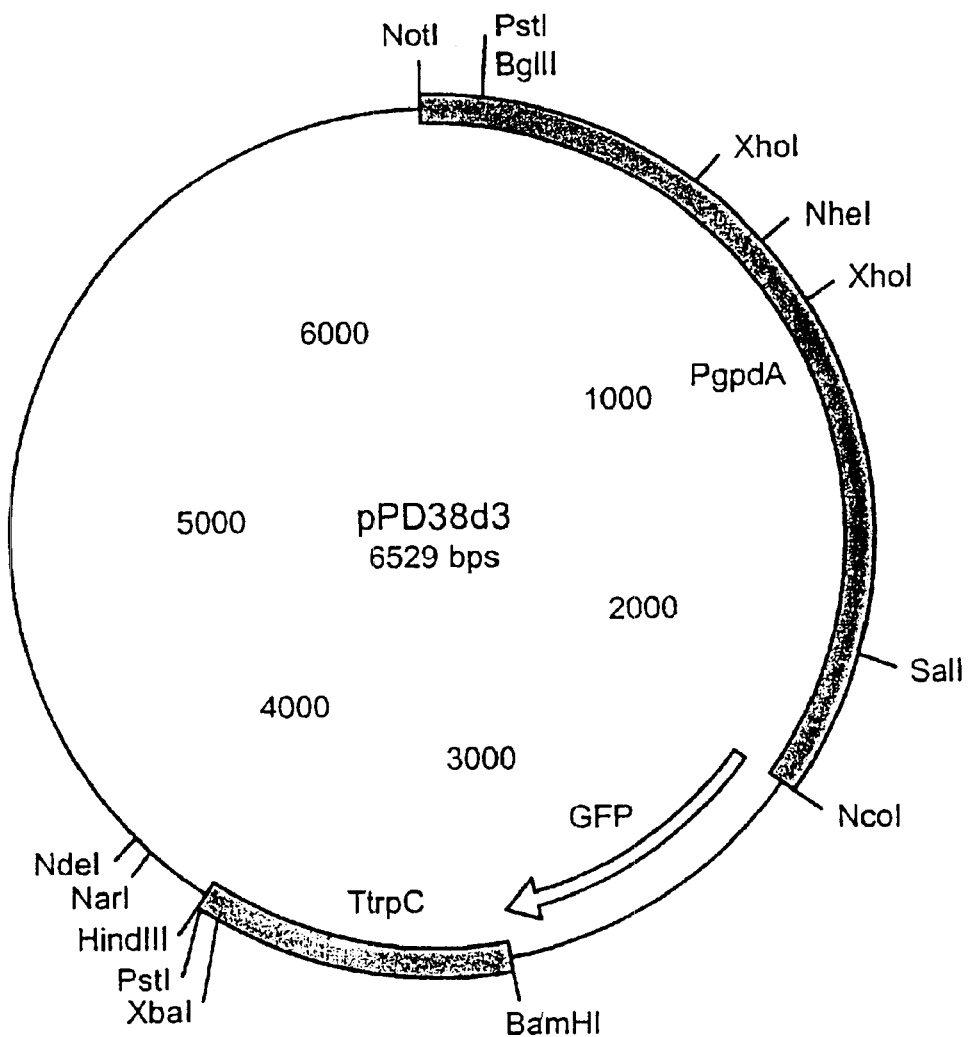
FIG. 7 is a representation of ppd38d3.

The CYPB protein contains a signal sequence and a putative ER retention signal, indicating that the protein is targeted and retained in the ER. However the retention signal in this protein is slightly divergent from the known retention signals. At position −3 (counting from the last amino acid residue) the CYPB protein contains a glutamic acid residue. This HEEL sequence has not been identified as an ER retention signal. To evaluate if this sequence is capable of retaining CYPB within the lumen of the ER, a GFP construct is made containing both the CYPB signal sequence and the CYPB ER retention signal. Expression of this gene is driven by the strong, constitutive gpdA promoter (plasmid pPD38d3; FIG. 7).

Transformants of the *Aspergillus niger* strain D15 (prtT; pyrG; phmA) are screened by PCR for insertion of the GFP expression plasmid. Strains containing the expression constructs are analysed for the expression of GFP.

Strain D15::pPD38d3#5 is grown overnight in liquid cultures and showed that GFP is directed to a tubular network within the cell. Equivalent constructs in A. nidulans have been demonstrated to target GFP to the ER, illuminating a network similar to our findings (Fernandez-Abalos, et al. (1998) Mol. Microbiol. 27, 121–130). Staining of hyphae with ER-Tracker DPX (Molecular Probes) illuminates the same type of tabular network.

Finally $DIOC_6$, a stain for mitochondria at low concentration, but also effective for ER staining when applied at higher concentrations, reveals the same tubular network as seen for DPX and GFP. $DIOC_6$ staining is however hampered by a diffusion of the stain out of the ER, resulting only in a staining of the mitochondria.

Our results show clearly that HEEL (SEQ ID NO: 8) is both necessary and sufficient for GFP retention in the ER. It is therefore clear that the CYPB protein is targeted to and retained in the ER,

What is claimed is:

1. A polypeptide possessing foldase activity characterised by having a capability to catalyse the cis-trans isomerisation of a peptide bond on the N terminal side of proline residues in polypeptides, having a signal sequence at the N-terminus and an endoplasmic reticulum retention signal at the C-terminus, and a molecular weight of 20.7 kDa and a deduced isoelectric point of 6.27.

2. A polypeptide according to claim 1, which is of fungal origin.

3. A polypeptide according to claim 2, which is derived from the genus Aspergillus.

4. A polypeptide according to claim 3, which is derived from *Aspergillus niger*.

5. A polypeptide possessing foldase activity characterised by having a capability to catalyse the cis-trans isomerisation of a peptide bond on the N terminal side of praline residues in polypeptides, encoded by a nucleic acid capable of hybridising under high stringency conditions with an oligonucleotide consisting of any 20 contiguous bases of SEQ ID No. 2, and wherein said polypeptide comprises a signal sequence at the N-terminus and an endoplasmic reticulum signal at the C-terminus.

6. A polypeptide possessing foldase activity characterised by having a capability to catalyse the cis-trans isomerisation of a peptide bond on the N terminal side of proline residues in polypeptides, encoded by a nucleic acid capable of hybridising under high stringency conditions with SEQ ID No. 1, and wherein said polypeptide comprises a signal sequence at the N-terminus and an endoplasmic reticulum signal at the C-terminus.

7. A polypeptide possessing foldase activity characterized by having a capability to catalyse the cis-trans isomerisation of a peptide bond on the N terminal side of proline residues in polypeptides, which is at least 80% homologous to SEQ. ID. No. 2, and wherein said polypeptide comprises a signal sequence at the N-terminus and an endoplasmic reticulum signal at the C-terminus.

* * * * *

SEQUENCE LISTING

```
<160> NUMBER OF SEQ ID NOS: 12

<210> SEQ ID NO 1
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1
ggyyavagyt crtcrtg                                                       17

<210> SEQ ID NO 2
<211> LENGTH: 987
<212> TYPE: DNA
<213> ORGANISM: Aspergillus niger
<220> FEATURE:
<221> NAME/KEY: CDS
<222> LOCATION: (42)..(677)

<400> SEQUENCE: 2
ggcacgagaa ttctcctaca ttggagacat cctgagcaat c atg aac ttc aag aac    56
                                              Met Asn Phe Lys Asn
                                                1               5 att ttt cta tct ttc ttc ttc gtc ctg gcg gtt gga ctt gct ctt gtc     104
Ile Phe Leu Ser Phe Phe Phe Val Leu Ala Val Gly Leu Ala Leu Val
             10                  15                  20 cac gcc gaa gat gct cag ccc cgg ggc ccc aag atc acc agt aag gtg     152
His Ala Glu Asp Ala Gln Pro Arg Gly Pro Lys Ile Thr Ser Lys Val
         25                  30                  35 ttc ttt gat ata gag cac gga gac aag cct ctg ggc aga gtc gtg ctt     200
Phe Phe Asp Ile Glu His Gly Asp Lys Pro Leu Gly Arg Val Val Leu
     40                  45                  50 ggc ttg tat ggc aag act gtt cct aag acc gct gag aac ttc cgg gct     248
Gly Leu Tyr Gly Lys Thr Val Pro Lys Thr Ala Glu Asn Phe Arg Ala
 55                  60                  65 ctc gct act ggt gag aag ggc ttt ggc tat gaa gga tct acc ttc cac     296
Leu Ala Thr Gly Glu Lys Gly Phe Gly Tyr Glu Gly Ser Thr Phe His
 70                  75                  80                  85 cgt gtc att aag gac ttc atg atc cag ggt ggt gac ttc act cgt ggc     344
Arg Val Ile Lys Asp Phe Met Ile Gln Gly Gly Asp Phe Thr Arg Gly
                 90                  95                 100 gat ggt acc ggt gga aag tcg atc tac ggt gag aag ttc gcc gac gaa     392
Asp Gly Thr Gly Gly Lys Ser Ile Tyr Gly Glu Lys Phe Ala Asp Glu
            105                 110                 115
```

```
aac ttc aag ctg agg cat acg cgc aag ggg ctc ctg agc atg gcc aac    440
Asn Phe Lys Leu Arg His Thr Arg Lys Gly Leu Leu Ser Met Ala Asn
        120                 125                 130 gcc ggc aag gac acc aac ggc tcc cag ttc ttc atc acc acc gtt cct    488
Ala Gly Lys Asp Thr Asn Gly Ser Gln Phe Phe Ile Thr Thr Val Pro
    135                 140                 145 aca cct tgg ctt gat ggc cgc cat gtc gtc ttc ggt gaa gtc ctc gag    536
Thr Pro Trp Leu Asp Gly Arg His Val Val Phe Gly Glu Val Leu Glu
150                 155                 160                 165 ggc tac gag atc gtc gct cag att gag aac gtg ccc aag ggc cgt tct    584
Gly Tyr Glu Ile Val Ala Gln Ile Glu Asn Val Pro Lys Gly Arg Ser
                170                 175                 180 gac aga ccc gtg gag act gtc aag atc gtc aag agt gga gag ttg gag    632
Asp Arg Pro Val Glu Thr Val Lys Ile Val Lys Ser Gly Glu Leu Glu
            185                 190                 195 tct gag gac aag gct gga gaa aaa ggt agc agc cac gag gag ctg        677
Ser Glu Asp Lys Ala Gly Glu Lys Gly Ser Ser His Glu Glu Leu
        200                 205                 210 tagacctgtt tcctgaggtc tcggccytgc ttctcgataa ractgtgaat gtgcydaacc   737
gcttkgtaaa gaaacgagct ccgaagaaga gtcacaacct tcagcaattg ctgttattcc   797
ttctccaacc cctttgccta tgacatctga taacgcycct tatattttcc cgaaattcgc   857
agcgcttgcc attgttgtcg gtcycctggt tgtcctggtc cgacgcagct caagggagaa   917
caagagaagg ctgaaagaag tattgtttga tagaaattgt actcatccaa wtaaaaaaaa   977
aaaaaaaaaa                                                         987

<210> SEQ ID NO 3
<211> LENGTH: 36
<212> TYPE: DNA
<213> ORGANISM: Artificial Sequence
<220> FEATURE:
<223> OTHER INFORMATION: Description of Artificial Sequence: Primer

<400> SEQUENCE: 3
cccatatgga agatgctcag ccccggggcc ccaaga                             36

<210> SEQ ID NO 4
<211> LENGTH: 43
<212> TYPE: DNA
<213> ORGANISM: Artificial Sequence
<220> FEATURE:
<223> OTHER INFORMATION: Description of Artificial Sequence: Primer

<400> SEQUENCE: 4
cgaagcttag tggtggtggt ggtggtggct gctacctttt tct                     43

<210> SEQ ID NO 5
<211> LENGTH: 212
<212> TYPE: PRT
<213> ORGANISM: Aspergillus niger

<400> SEQUENCE: 5

Met Asn Phe Lys Asn Ile Phe Leu Ser Phe Phe Val Leu Ala Val
 1               5                  10                  15

Gly Leu Ala Leu Val His Ala Glu Asp Ala Gln Pro Arg Gly Pro Lys
                20                  25                  30

Ile Thr Ser Lys Val Phe Phe Asp Ile Glu His Gly Asp Lys Pro Leu
            35                  40                  45

Gly Arg Val Val Leu Gly Leu Tyr Gly Lys Thr Val Pro Lys Thr Ala
        50                  55                  60
```

```
Glu Asn Phe Arg Ala Leu Ala Thr Gly Glu Lys Gly Phe Gly Tyr Glu
 65                  70                  75                  80

Gly Ser Thr Phe His Arg Val Ile Lys Asp Phe Met Ile Gln Gly Gly
             85                  90                  95

Asp Phe Thr Arg Gly Asp Gly Thr Gly Gly Lys Ser Ile Tyr Gly Glu
        100                 105                 110

Lys Phe Ala Asp Glu Asn Phe Lys Leu Arg His Thr Arg Lys Gly Leu
    115                 120                 125

Leu Ser Met Ala Asn Ala Gly Lys Asp Thr Asn Gly Ser Gln Phe Phe
    130                 135                 140

Ile Thr Thr Val Pro Thr Pro Trp Leu Asp Gly Arg His Val Val Phe
145                 150                 155                 160

Gly Glu Val Leu Glu Gly Tyr Glu Ile Val Ala Gln Ile Glu Asn Val
                165                 170                 175

Pro Lys Gly Arg Ser Asp Arg Pro Val Glu Thr Val Lys Ile Val Lys
            180                 185                 190

Ser Gly Glu Leu Glu Ser Glu Asp Lys Ala Gly Glu Lys Gly Ser Ser
        195                 200                 205

His Glu Glu Leu
    210
```

<210> SEQ ID NO 6
<211> LENGTH: 1834
<212> TYPE: DNA
<213> ORGANISM: Aspergillus niger
<220> FEATURE:
<221> NAME/KEY: modified_base
<222> LOCATION: (3)
<223> OTHER INFORMATION: a, t, c, g, other or unknown

<400> SEQUENCE: 6

```
ccndttaatc ccccaccggg gttcccgctc ccggatggag atggggccaa aactggcaac      60
ccccagttgc gcaacggaac aaccgccgac ccggaacaaa ggatgcggat gaggagatac     120
ggtgcctgat tgcatggctg gcttcatctg ctatcgtgac agtgctcttt gggtgaatat     180
tgttgtctga cttaccccgc ttcttgcttt ttcccccctg aggccctgat ggggaatcgc     240
ggtgggtaat atgatatggg tataaaaggg agatcggagg tgcagttgga ttgaggcagt     300
gtgtgtgtgt gcattgcaga agcccgttgg tcgcaaggtt ttggtcgcct cgattgtttg     360
tataccgcaa gatgttctct ggacggtttg gagtgctttt gacagcgctt gctgcgctgg     420
gtgctgccgc gccggcaccg cttgctgtgc ggagtaggtg tgcccgatgt gagatggttg     480
gatagcactg atgaagggtg aataggtgtc tcgacttcca cgttggatga gttgcaattg     540
ttcgcgcaat ggtctgccgc agcttattgc tcgaataata tcgactcgaa agactccaac     600
ttgacatgca cggccaacgc ctgtccatca gtcgaggagg ccagtaccac gatgctgctg     660
gagttcgacc tgtatgtcac tcagatcgca gacatagagc acagctaatt gaacaggac      720
gaacgacttt ggaggcacag ccggtttcct ggccgcggac aacaccaaca agcggctcgt     780
ggtcgccttc cggggaagca gcacgattga aactggatt  gctaatcttg acttcatcct     840
ggaagataac gacgacctct gcaccggctg caaggtccat actggtttct ggaaggcatg     900
ggagtccgct gccgacgaac tgacgagcaa gatcaagtct gcgatgagca cgtattcggg     960
ctataccccta tacttcaccg ggcacagttt gggcggcgca ttggctacgc tgggagcgac    1020
agttctgcga aatgacggat atagcgttga gctggtgagt cctcacaaa ggtgatggag     1080
```

```
cgacaatcgg gttctgacag tcaatagtac acctatggat gtcctcgaat cggaaactat    1140
gcgctggctg agcatatcac cagtcaggga tctggggcca acttccgtgt tacacacttg    1200
aacgacatcg tcccccgggt gccacccatg gactttggat tcagtcagcc aagtccggaa    1260
tactggatca ccagtggcaa tggagccagt gtcacggcgt cggatatcga agtcatcgag    1320
ggaatcaatt caacggcggg aaatgcaggc gaagcaacgg tgagcgttgt ggctcacttg    1380
tggtactttt ttgcgatttc cgagtgcctg ctataactag accgactgtc agattagtgg    1440
acgggagaag tgtacataag taattagtat ataatcagag caacccagtg gtggtgatgg    1500
tggtgaaaga agaaacacat tgagttccca ttacgkagca gwtaaagcac ktkkggaggc    1560
gctggttcct ccacttggca gttggcggcc atcaatcatc tttcctctcc ttactttcgt    1620
ccaccacaac tcccatcctg ccagctgtcg catccccggg ttgcaacaac tatcgcctcc    1680
ggggcctccg tggttctcct atattattcc atccgacggc cgacgtttca ccctcaacct    1740
gcgccgccgc aaaatctccc cgagtcggtc aactccctcg aaccgccgcc cgcatcgacc    1800
tcaccgaccc cgaccgtctg ygatygtcca accg                                1834
```

```
<210> SEQ ID NO 7
<211> LENGTH: 4
<212> TYPE: PRT
<213> ORGANISM: Artificial Sequence
<220> FEATURE:
<223> OTHER INFORMATION: Description of Artificial Sequence: Illustrative ER
      retention
      signal

<400> SEQUENCE: 7

His Asp Glu Leu
  1

<210> SEQ ID NO 8
<211> LENGTH: 4
<212> TYPE: PRT
<213> ORGANISM: Artificial Sequence
<220> FEATURE:
<223> OTHER INFORMATION: Description of Artificial Sequence: Illustrative ER
      retention
      signal

<400> SEQUENCE: 8

His Glu Glu Leu
  1

<210> SEQ ID NO 9
<211> LENGTH: 4
<212> TYPE: PRT
<213> ORGANISM: Artificial Sequence
<220> FEATURE:
<223> OTHER INFORMATION: Description of Artificial Sequence: Illustrative ER
      retention
      signal

<400> SEQUENCE: 9

Lys Asp Glu Leu
  1

<210> SEQ ID NO 10
<211> LENGTH: 203
<212> TYPE: PRT
<213> ORGANISM: Orpinomyces sp.

<400> SEQUENCE: 10
```

```
Met Asn Phe Ser Ile Lys Ser Val Ile Phe Leu Ala Ile Val Ala Leu
  1               5                  10                  15

Ala Thr Leu Val Ser Ala Ser Thr Asn Pro Lys Val Thr Asn Lys Val
             20                  25                  30

Tyr Phe Asp Ile Lys Gln Gly Asp Lys Asp Leu Gly Arg Ile Val Leu
             35                  40                  45

Gly Leu Tyr Gly Glu Val Pro Lys Thr Val Glu Asn Phe Arg Ala
 50                  55                  60

Leu Ala Thr Gly Glu Lys Gly Tyr Gly Tyr Lys Asn Ser Lys Phe His
 65                  70                  75                  80

Arg Val Ile Lys Asp Phe Met Ile Gln Gly Asp Phe Thr Arg Gly
             85                  90                  95

Asp Gly Thr Gly Gly Lys Ser Ile Tyr Gly Arg Phe Ala Asp Glu
            100                 105                 110

Asn Phe Lys Leu Arg His Thr Gly Pro Gly Ile Leu Ser Met Ala Asn
            115                 120                 125

Ala Gly Arg Asp Thr Asn Gly Ser Gln Phe Phe Ile Thr Thr Val Thr
130                 135                 140

Thr Ser Trp Leu Asp Gly Arg His Val Val Phe Gly Lys Val Ile Glu
145                 150                 155                 160

Gly Met Asp Val Val Thr Ala Ile Glu Thr Thr Lys Thr Leu Pro Gly
                165                 170                 175

Asp Arg Pro Ala Thr Pro Val Ile Ile Ala Asp Cys Gly Glu Leu Pro
            180                 185                 190

Val Ser Asn Asn Asn Asp Ala Lys Ala Glu Leu
            195                 200

<210> SEQ ID NO 11
<211> LENGTH: 207
<212> TYPE: PRT
<213> ORGANISM: Mus musculus

<400> SEQUENCE: 11

Met Lys Ala Leu Val Ala Ala Thr Ala Leu Gly Pro Ala Leu Leu Leu
  1               5                  10                  15

Leu Leu Pro Ala Ala Ser Arg Ala Asp Glu Arg Lys Lys Gly Pro Lys
             20                  25                  30

Val Thr Ala Lys Val Phe Phe Asp Leu Arg Val Gly Glu Glu Asp Ala
             35                  40                  45

Gly Arg Val Val Ile Gly Leu Phe Gly Lys Thr Val Pro Lys Thr Val
 50                  55                  60

Glu Asn Phe Val Ala Leu Ala Thr Gly Glu Lys Gly Phe Gly Phe Lys
 65                  70                  75                  80

Gly Ser Lys Phe His Arg Val Ile Lys Asp Phe Met Ile Gln Gly Gly
             85                  90                  95

Asp Phe Thr Arg Gly Asp Gly Thr Gly Gly Lys Ser Ile Tyr Gly Asp
            100                 105                 110

Arg Phe Pro Asp Glu Asn Phe Lys Leu Lys His Tyr Gly Pro Gly Trp
            115                 120                 125

Val Ser Met Ala Asn Ala Gly Lys Asp Thr Asn Gly Ser Gln Phe Phe
130                 135                 140

Ile Thr Thr Val Lys Thr Ala Trp Leu Asp Gly Lys His Val Val Phe
145                 150                 155                 160

Gly Lys Val Leu Glu Gly Met Asp Val Val Arg Lys Val Glu Asn Thr
                165                 170                 175
```

-continued

```
Lys Thr Asp Ser Arg Asp Lys Pro Leu Lys Asp Val Thr Ile Ala Asp
            180                 185                 190

Cys Gly Thr Ile Glu Val Glu Lys Pro Phe Ala Ile Ala Lys Glu
        195                 200                 205

<210> SEQ ID NO 12
<211> LENGTH: 208
<212> TYPE: PRT
<213> ORGANISM: Homo sapiens

<400> SEQUENCE: 12

Met Lys Val Leu Leu Ala Ala Leu Ile Ala Gly Ser Val Phe Phe
 1               5                  10                  15

Leu Leu Leu Pro Gly Pro Ser Ala Ala Asp Glu Lys Lys Lys Gly Pro
            20                  25                  30

Lys Val Thr Val Lys Val Tyr Phe Asp Leu Arg Ile Gly Asp Glu Asp
            35                  40                  45

Val Gly Arg Val Ile Phe Gly Leu Phe Gly Lys Thr Val Pro Lys Thr
        50                  55                  60

Val Asp Asn Phe Val Ala Leu Ala Thr Gly Glu Lys Gly Phe Gly Tyr
 65                  70                  75                  80

Lys Asn Ser Lys Phe His Arg Val Ile Lys Asp Phe Met Ile Gln Gly
                85                  90                  95

Gly Asp Phe Thr Arg Gly Asp Gly Thr Gly Gly Lys Ser Ile Tyr Gly
                100                 105                 110

Glu Arg Phe Pro Asp Glu Asn Phe Lys Leu Lys His Tyr Gly Pro Gly
            115                 120                 125

Trp Val Ser Met Ala Asn Ala Gly Lys Asp Thr Asn Gly Ser Gln Phe
        130                 135                 140

Phe Ile Thr Thr Val Lys Thr Ala Trp Leu Asp Gly Lys His Val Val
145                 150                 155                 160

Phe Gly Lys Val Leu Glu Gly Met Glu Val Val Arg Lys Val Glu Ser
                165                 170                 175

Thr Lys Thr Asp Ser Arg Asp Lys Pro Leu Lys Asp Val Ile Ile Ala
            180                 185                 190

Asp Cys Gly Lys Ile Glu Val Glu Lys Pro Phe Ala Ile Ala Lys Glu
        195                 200                 205
```